United States Patent
Slazas et al.

(10) Patent No.: US 11,357,648 B2
(45) Date of Patent: Jun. 14, 2022

(54) SYSTEMS AND METHODS OF USING A BRAIDED IMPLANT

(71) Applicant: DePuy Synthes Products, Inc., Raynham, MA (US)

(72) Inventors: Robert Slazas, Raynham, MA (US); Geoff Peters, Raynham, MA (US)

(73) Assignee: DePuy Synthes Products, Inc.

(*) Notice: Subject to any disclaimer, the term of this patent is extended or adjusted under 35 U.S.C. 154(b) by 0 days.

(21) Appl. No.: 16/597,420

(22) Filed: Oct. 9, 2019

(65) Prior Publication Data
US 2020/0046526 A1 Feb. 13, 2020

Related U.S. Application Data

(62) Division of application No. 16/056,135, filed on Aug. 6, 2018, now Pat. No. 10,456,280.

(51) Int. Cl.
*A61F 2/88* (2006.01)
*A61L 31/14* (2006.01)
(Continued)

(52) U.S. Cl.
CPC .......... *A61F 2/88* (2013.01); *A61F 2/07* (2013.01); *A61F 2/844* (2013.01); *A61F 2/92* (2013.01);
(Continued)

(58) Field of Classification Search
CPC .......... A61F 2/06; A61F 2002/067; A61F 2002/068; A61F 2/07; A61F 2002/072;
(Continued)

(56) References Cited

U.S. PATENT DOCUMENTS

| | | |
|---|---|---|
| 4,332,278 A | 4/1982 | Lalikos |
| 4,610,688 A | 9/1986 | Silvestrini |

(Continued)

FOREIGN PATENT DOCUMENTS

| | | |
|---|---|---|
| CN | 101234046 A | 8/2008 |
| CN | 101779992 A | 7/2010 |

(Continued)

OTHER PUBLICATIONS

Ansaar T. Rai et al., "Cerebrovascular geometry in the anterior circulation: an analysis of diameter, length and the vessel taper", J NeuroIntervent Surg 2013; 5: 371-375_ doi: 10_ 1136/neurintsurg-2012-010314; Apr. 4, 2012 cited in parent U.S. Appl. No. 16/056,135.

(Continued)

*Primary Examiner* — Paul B Prebilic
(74) *Attorney, Agent, or Firm* — Troutman Pepper Hamilton Sanders LLP

(57) ABSTRACT

A method of treating an aneurysm, including determining a diameter associated with a vessel having the aneurysm; selecting one of a plurality of braided implants for treating the vessel, wherein each braided implant comprises a porosity substantially consistent over up to a 1 mm diameter range, each braided implant configured to provide consistent porosity over different diameter ranges; and treating the vessel with the one of the plurality of braided implants.

20 Claims, 8 Drawing Sheets

(51) Int. Cl.
   *A61F 2/07* (2013.01)
   *A61F 2/92* (2013.01)
   *A61F 2/95* (2013.01)
   *A61F 2/844* (2013.01)

(52) U.S. Cl.
   CPC ............. *A61F 2/95* (2013.01); *A61L 31/146* (2013.01); *A61F 2/9522* (2020.05); *A61F 2002/9534* (2013.01)

(58) Field of Classification Search
   CPC ...... A61F 2002/077; A61F 2/844; A61F 2/92; A61F 2/95; A61F 2/9522; A61F 2002/9534; A61F 2230/0069; A61F 2230/0067; A61F 2250/0026; A61F 2250/0029; A61F 2250/0032; A61F 2250/0039; A61F 2250/0064; A61F 2250/0098
   See application file for complete search history.

(56) References Cited

U.S. PATENT DOCUMENTS

| | | | |
|---|---|---|---|
| 4,754,685 | A | 7/1988 | Kite |
| 5,064,435 | A | 11/1991 | Porter |
| 5,275,622 | A * | 1/1994 | Lazarus ............... A61B 17/11 604/103.02 |
| 5,282,824 | A | 2/1994 | Gianturco |
| 5,330,500 | A | 7/1994 | Song |
| 5,382,259 | A | 1/1995 | Phelps et al. |
| 5,387,235 | A | 2/1995 | Chuter |
| 5,423,849 | A | 6/1995 | Engelson |
| 5,476,508 | A | 12/1995 | Amstrup |
| 5,522,881 | A | 6/1996 | Lentz |
| 5,549,662 | A | 8/1996 | Fordenbacher |
| 5,556,413 | A | 9/1996 | Lam |
| 5,601,593 | A | 2/1997 | Freitag |
| 5,609,627 | A | 3/1997 | Goicoechea |
| 5,645,558 | A | 7/1997 | Horton |
| 5,662,622 | A | 9/1997 | Gore et al. |
| 5,702,418 | A | 12/1997 | Ravenscroft |
| 5,725,549 | A | 3/1998 | Lam |
| 5,728,131 | A | 3/1998 | Frantzen |
| 5,755,772 | A | 5/1998 | Evans et al. |
| 5,769,887 | A | 6/1998 | Brown |
| 5,776,161 | A | 7/1998 | Globerman |
| 5,817,126 | A | 10/1998 | Imran |
| 5,849,037 | A | 12/1998 | Frid |
| 5,851,217 | A | 12/1998 | Wolff |
| 5,855,601 | A | 1/1999 | Bessler |
| 5,899,935 | A | 5/1999 | Ding |
| 5,916,235 | A | 6/1999 | Guglielmi |
| 5,916,264 | A | 6/1999 | Von Oepen |
| 5,961,546 | A | 10/1999 | Robinson et al. |
| 6,010,529 | A | 1/2000 | Herweck |
| 6,015,432 | A | 1/2000 | Rakos et al. |
| 6,033,436 | A | 3/2000 | Steinke |
| 6,036,725 | A | 3/2000 | Avellanet |
| 6,051,020 | A | 4/2000 | Goicoechea |
| 6,099,559 | A | 8/2000 | Nolting |
| 6,110,198 | A | 8/2000 | Fogarty et al. |
| 6,123,722 | A | 9/2000 | Fogarty et al. |
| 6,123,723 | A | 9/2000 | Konya et al. |
| 6,152,956 | A | 11/2000 | Pierce |
| 6,161,399 | A | 12/2000 | Jayaraman |
| 6,165,213 | A | 12/2000 | Goicoechea |
| 6,168,621 | B1 | 1/2001 | Vrba |
| 6,176,875 | B1 | 1/2001 | Lenker |
| 6,264,683 | B1 | 7/2001 | Stack et al. |
| 6,280,465 | B1 | 8/2001 | Cryer |
| 6,319,278 | B1 | 11/2001 | Quinn |
| 6,325,823 | B1 | 12/2001 | Horzewski |
| 6,348,066 | B1 * | 2/2002 | Pinchuk .................. A61F 2/07 606/198 |
| 6,391,037 | B1 | 5/2002 | Greenhalgh |
| 6,409,755 | B1 | 6/2002 | Vrba |
| 6,488,702 | B1 | 12/2002 | Besselink |
| 6,612,012 | B2 | 9/2003 | Mitelberg et al. |
| 6,626,936 | B2 | 9/2003 | Stinson |
| 6,635,080 | B1 | 10/2003 | Lauterjung et al. |
| 6,673,106 | B2 | 1/2004 | Mitelberg |
| 6,699,277 | B1 | 3/2004 | Freidberg et al. |
| 6,740,113 | B2 | 5/2004 | Vrba |
| 6,673,107 | B1 | 6/2004 | Brandt |
| 6,770,089 | B1 | 8/2004 | Hong et al. |
| 6,818,013 | B2 | 11/2004 | Mitelberg |
| 6,833,003 | B2 | 12/2004 | Jones |
| 6,899,914 | B2 | 5/2005 | Schmitz |
| 6,911,040 | B2 | 6/2005 | Johnson et al. |
| 6,918,928 | B2 | 7/2005 | Wolinsky |
| 6,929,659 | B2 | 8/2005 | Pinchuk |
| 6,945,994 | B2 | 9/2005 | Austin et al. |
| 6,955,685 | B2 | 10/2005 | Escamilla |
| 6,960,227 | B2 | 11/2005 | Jones |
| 6,960,228 | B2 | 11/2005 | Mitelberg et al. |
| 6,970,734 | B2 | 11/2005 | Eidenschink |
| 7,001,422 | B2 | 2/2006 | Escamilla |
| 7,037,331 | B2 | 5/2006 | Mitelberg |
| 7,122,052 | B2 | 10/2006 | Greenhaigh |
| 7,153,324 | B2 | 12/2006 | Case |
| 7,201,769 | B2 | 4/2007 | Jones et al. |
| 7,208,008 | B2 | 4/2007 | Clarke |
| 7,267,685 | B2 | 9/2007 | Butaric |
| 7,288,111 | B1 | 10/2007 | Holloway et al. |
| 7,291,167 | B2 | 11/2007 | DiCaprio |
| 7,309,351 | B2 | 12/2007 | Escamilla et al. |
| 7,344,559 | B2 | 3/2008 | Gray |
| 7,462,190 | B2 | 12/2008 | Lombardi |
| 7,480,973 | B2 | 1/2009 | Miller |
| 7,628,806 | B2 | 12/2009 | Yampolsky et al. |
| 7,632,302 | B2 | 12/2009 | Vreeman et al. |
| 7,641,647 | B2 | 1/2010 | Gunderson |
| 7,655,031 | B2 | 2/2010 | Tenne et al. |
| 7,655,034 | B2 | 2/2010 | Mitchell et al. |
| 7,708,773 | B2 | 5/2010 | Pinchuk et al. |
| 7,758,629 | B2 | 7/2010 | Holloway et al. |
| 7,761,138 | B2 | 7/2010 | Wang |
| 7,806,919 | B2 | 10/2010 | Bloom et al. |
| 7,806,923 | B2 | 10/2010 | Moloney |
| RE42,244 | E | 3/2011 | Boatman |
| 7,913,371 | B2 | 3/2011 | Klocke |
| 7,985,213 | B2 | 7/2011 | Parker |
| 7,998,187 | B2 | 8/2011 | Hartley et al. |
| 8,021,418 | B2 | 9/2011 | Gerberding |
| 8,043,353 | B2 | 10/2011 | Kaufmann et al. |
| 8,043,357 | B2 | 10/2011 | Hartley |
| 8,048,139 | B2 | 11/2011 | Frid et al. |
| 8,052,741 | B2 | 11/2011 | Bruszewski et al. |
| 8,092,510 | B2 | 1/2012 | Metcalf et al. |
| 8,142,456 | B2 | 3/2012 | Rosqueta |
| 8,152,833 | B2 | 4/2012 | Zaver |
| 8,182,523 | B2 | 5/2012 | Tenne et al. |
| 8,187,316 | B2 | 5/2012 | Kuppurathanam |
| 8,357,194 | B2 | 1/2013 | Majercak |
| 8,372,133 | B2 | 2/2013 | Douk et al. |
| 8,394,119 | B2 | 3/2013 | Zaver |
| 8,449,600 | B2 | 5/2013 | Hartley et al. |
| 8,449,604 | B2 | 5/2013 | Moaddeb |
| 8,484,120 | B2 | 7/2013 | Hagaman et al. |
| 8,562,666 | B2 | 10/2013 | Bonsignore |
| 8,579,959 | B2 | 11/2013 | Ducke |
| 8,597,276 | B2 | 12/2013 | Vongphakdy et al. |
| 8,641,748 | B2 | 2/2014 | Hebert et al. |
| 8,672,992 | B2 | 3/2014 | Orr |
| 8,709,065 | B2 | 4/2014 | Chobotov |
| 8,734,501 | B2 | 5/2014 | Hartley et al. |
| 8,778,008 | B2 | 7/2014 | Amplatz et al. |
| 8,816,247 | B1 | 8/2014 | Janardhan et al. |
| 8,864,811 | B2 | 10/2014 | Kao |
| 9,078,731 | B2 | 7/2015 | Mortarino |
| 9,192,462 | B2 | 11/2015 | Vinluan et al. |
| 9,232,992 | B2 | 1/2016 | Heidner |
| 9,301,864 | B2 | 4/2016 | Kao |
| 9,320,590 | B2 | 4/2016 | Zaver |

(56) References Cited

U.S. PATENT DOCUMENTS

| | | |
|---|---|---|
| 9,339,260 B2 | 5/2016 | Eidenschink et al. |
| 9,427,343 B2 | 8/2016 | Bogert |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,713,523 B2 | 7/2017 | Zacharias |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,787,260 B2 | 10/2017 | Lehtola |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,004,513 B2 | 6/2018 | Leopold et al. |
| 10,058,421 B2 | 8/2018 | Eberhardt et al. |
| 10,076,428 B2 | 9/2018 | Gorochow |
| 10,143,551 B2 | 12/2018 | Braido et al. |
| 10,182,927 B2 | 1/2019 | Lorenzo |
| 10,206,796 B2 | 2/2019 | Tehrani et al. |
| 10,232,564 B2 | 5/2019 | Pelled |
| 10,292,851 B2 | 5/2019 | Gorochow |
| 10,321,991 B2 | 6/2019 | Glimsdale |
| 10,561,509 B2 | 2/2020 | Slazas et al. |
| 10,821,008 B2 | 11/2020 | Gorochow |
| 2001/0021873 A1 | 9/2001 | Stinson |
| 2001/0025195 A1 | 9/2001 | Shaolian |
| 2001/0049554 A1 | 12/2001 | Ruiz et al. |
| 2002/0095205 A1 | 7/2002 | Edwin |
| 2002/0111671 A1 | 8/2002 | Stenzel |
| 2002/0151953 A1 | 10/2002 | Chobotov |
| 2002/0151956 A1 | 10/2002 | Chobotov |
| 2002/0198587 A1 | 12/2002 | Greenberg et al. |
| 2003/0009211 A1 | 1/2003 | DiCarlo |
| 2003/0055493 A1 | 3/2003 | Carpenter |
| 2003/0114922 A1 | 6/2003 | Iwasaka |
| 2003/0144725 A1 | 7/2003 | Lombardi |
| 2004/0015229 A1 | 1/2004 | Fulkerson |
| 2004/0024416 A1 | 2/2004 | Yodfat et al. |
| 2004/0044399 A1 | 3/2004 | Ventura |
| 2004/0073291 A1 | 4/2004 | Brown |
| 2004/0167619 A1 | 8/2004 | Case |
| 2004/0254637 A1 | 12/2004 | Vang |
| 2005/0010281 A1 | 1/2005 | Yodfat et al. |
| 2005/0033406 A1 | 2/2005 | Barnhart |
| 2005/0043784 A1 | 2/2005 | Yampolsky et al. |
| 2005/0049668 A1 | 3/2005 | Jones et al. |
| 2005/0049669 A1 | 3/2005 | Jones et al. |
| 2005/0049670 A1 | 3/2005 | Jones |
| 2005/0125051 A1 | 6/2005 | Eidenschink |
| 2005/0131516 A1 | 6/2005 | Greenhalgh |
| 2005/0137682 A1 | 6/2005 | Justino |
| 2005/0148866 A1 | 7/2005 | Gunderson |
| 2005/0228484 A1 | 10/2005 | Stephens et al. |
| 2005/0234536 A1 | 10/2005 | Mitelberg |
| 2005/0257674 A1 | 11/2005 | Nishri et al. |
| 2005/0283220 A1 | 12/2005 | Gobran |
| 2005/0288775 A1 | 12/2005 | Dong |
| 2006/0015173 A1 | 1/2006 | Clifford |
| 2006/0064151 A1 | 3/2006 | Guterman |
| 2006/0064156 A1 | 3/2006 | Thistle |
| 2006/0069424 A1 | 3/2006 | Acosta |
| 2006/0195175 A1 | 8/2006 | Bregulla |
| 2006/0206202 A1 | 9/2006 | Bonhoeffer et al. |
| 2006/0212113 A1 | 9/2006 | Shaolian et al. |
| 2006/0271153 A1 | 11/2006 | Garcia |
| 2006/0271165 A1 | 11/2006 | Yip et al. |
| 2006/0287717 A1 | 12/2006 | Rowe |
| 2007/0043432 A1 | 2/2007 | Perouse |
| 2007/0060994 A1 | 3/2007 | Gobran |
| 2007/0100427 A1 | 5/2007 | Perouse |
| 2007/0156230 A1 | 7/2007 | Dugan |
| 2007/0167955 A1 | 7/2007 | Arnault De La Menardiere et al. |
| 2007/0191922 A1 | 8/2007 | Hartley |
| 2007/0203503 A1 | 8/2007 | Salahieh |
| 2007/0208373 A1 | 9/2007 | Zaver et al. |
| 2007/0208409 A1 | 9/2007 | Quigley |
| 2007/0213810 A1 | 9/2007 | Newhauser |
| 2007/0219613 A1 | 9/2007 | Kao |
| 2007/0233223 A1 | 10/2007 | Styrc |
| 2007/0233224 A1 | 10/2007 | Leynov |
| 2007/0233228 A1 | 10/2007 | Eberhardt et al. |
| 2007/0238979 A1 | 10/2007 | Huynh |
| 2007/0255385 A1 | 11/2007 | Tenne et al. |
| 2008/0009934 A1 | 1/2008 | Schneider et al. |
| 2008/0009938 A1 | 1/2008 | Huang |
| 2008/0071307 A1 | 3/2008 | DeBruyne et al. |
| 2008/0140172 A1 | 6/2008 | Carpenter |
| 2008/0221664 A1 | 9/2008 | Bales et al. |
| 2008/0221670 A1 | 9/2008 | Clerc |
| 2008/0243227 A1 | 10/2008 | Lorenzo |
| 2008/0281350 A1 | 11/2008 | Sepetka |
| 2008/0288046 A1 | 11/2008 | Hemerick |
| 2009/0005848 A1 | 1/2009 | Strauss |
| 2009/0030501 A1 | 1/2009 | Morris |
| 2009/0076594 A1 | 3/2009 | Sabaria |
| 2009/0082844 A1 | 3/2009 | Zacharias |
| 2009/0082845 A1 | 3/2009 | Chobotov |
| 2009/0082847 A1 | 3/2009 | Zacharias |
| 2009/0163951 A1 | 6/2009 | Simmons |
| 2009/0198315 A1 | 8/2009 | Boudjemline |
| 2009/0234429 A1 | 9/2009 | Lau |
| 2009/0287145 A1 | 11/2009 | Cragg |
| 2009/0297582 A1* | 12/2009 | Meyer ............ A61B 17/12113 424/423 |
| 2009/0306761 A1 | 12/2009 | Hebert et al. |
| 2009/0326640 A1 | 12/2009 | Yoshimura |
| 2010/0010619 A1 | 1/2010 | Tischler |
| 2010/0069948 A1 | 3/2010 | Veznedaroglu |
| 2010/0161028 A1 | 6/2010 | Chuter |
| 2010/0249815 A1 | 9/2010 | Jantzen |

(56) References Cited

U.S. PATENT DOCUMENTS

| | | |
|---|---|---|
| 2010/0292777 A1 | 11/2010 | Meyer |
| 2010/0298872 A1 | 11/2010 | Berndt |
| 2010/0324649 A1 | 12/2010 | Mattsson |
| 2010/0324651 A1 | 12/2010 | Holzer |
| 2010/0331972 A1 | 12/2010 | Pintor |
| 2011/0004237 A1 | 1/2011 | Schneider et al. |
| 2011/0060400 A1 | 3/2011 | Oepen |
| 2011/0137397 A1 | 6/2011 | Chan et al. |
| 2011/0184508 A2 | 7/2011 | Burmeister |
| 2011/0264186 A1 | 10/2011 | Berglung et al. |
| 2011/0307049 A1 | 12/2011 | Kao |
| 2012/0035714 A1 | 2/2012 | Ducke et al. |
| 2012/0041538 A1 | 2/2012 | White |
| 2012/0065728 A1 | 3/2012 | Galnor et al. |
| 2012/0123529 A1 | 5/2012 | Levi |
| 2012/0168022 A1 | 7/2012 | Rasmussen |
| 2012/0191176 A1 | 7/2012 | Nagl |
| 2012/0197377 A1 | 8/2012 | Ditter |
| 2012/0271403 A1 | 10/2012 | Gries |
| 2012/0283768 A1 | 11/2012 | Cox et al. |
| 2012/0296418 A1 | 11/2012 | Bonyuet |
| 2013/0041454 A1 | 2/2013 | Dobson |
| 2013/0060323 A1 | 3/2013 | McHugo |
| 2013/0123901 A1 | 5/2013 | Connor |
| 2013/0144375 A1 | 6/2013 | Giasolli |
| 2013/0245745 A1 | 9/2013 | Vong et al. |
| 2013/0253572 A1 | 9/2013 | Molaei et al. |
| 2013/0274849 A1 | 10/2013 | Zaver |
| 2013/0345739 A1 | 12/2013 | Brady |
| 2014/0025161 A1 | 1/2014 | Stankus et al. |
| 2014/0135812 A1 | 5/2014 | Divino et al. |
| 2014/0200607 A1 | 7/2014 | Sepetka et al. |
| 2014/0200648 A1 | 7/2014 | Newell et al. |
| 2014/0277332 A1 | 9/2014 | Slazas et al. |
| 2014/0277360 A1 | 9/2014 | Girnary et al. |
| 2014/0277376 A1 | 9/2014 | Lorenzo |
| 2014/0277400 A1 | 9/2014 | Wainwright et al. |
| 2014/0336741 A1 | 11/2014 | Connor |
| 2015/0018458 A1 | 1/2015 | Ito |
| 2015/0025625 A1 | 1/2015 | Rylski et al. |
| 2015/0045831 A1 | 2/2015 | Allen |
| 2015/0119974 A1 | 4/2015 | Rothstein |
| 2015/0148882 A1 | 5/2015 | Ma et al. |
| 2015/0265400 A1 | 9/2015 | Eidenschink |
| 2015/0320556 A1 | 11/2015 | Levi |
| 2015/0374483 A1 | 12/2015 | Janardham et al. |
| 2016/0030155 A1 | 2/2016 | Cox et al. |
| 2016/0038280 A1 | 2/2016 | Morriss |
| 2016/0058524 A1* | 3/2016 | Tehrani .................. A61F 2/07 623/1.34 |
| 2016/0235561 A1 | 8/2016 | Wrobel et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079813 A1 | 3/2017 | Bar et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0156734 A1 | 6/2017 | Griffin |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0196689 A1 | 7/2017 | Salahieh |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265870 A1 | 9/2017 | Kealey et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281375 A1 | 10/2017 | Longo |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290653 A1 | 10/2017 | Folan et al. |
| 2017/0290654 A1 | 10/2017 | Sethna |
| 2017/0290686 A1 | 10/2017 | Sirhan |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0092766 A1 | 4/2018 | Gorochow |
| 2018/0125649 A1 | 5/2018 | Nasr |
| 2018/0263794 A1 | 9/2018 | Slazas et al. |
| 2018/0333281 A1 | 11/2018 | Tehrani et al. |
| 2019/0015229 A1 | 1/2019 | Fukutaki |
| 2019/0021888 A1 | 1/2019 | Tehrani |
| 2019/0038404 A1 | 2/2019 | Iamberger |
| 2019/0038405 A1 | 2/2019 | Iamberger |
| 2019/0053895 A1 | 2/2019 | Levi |
| 2019/0053899 A1 | 2/2019 | Levi |

FOREIGN PATENT DOCUMENTS

| | | |
|---|---|---|
| CN | 102100587 A | 6/2011 |
| CN | 102271620 A | 12/2011 |
| CN | 103330605 A | 10/2013 |
| CN | 104042376 A | 9/2014 |
| CN | 104042380 A | 9/2014 |
| CN | 104582643 A | 4/2015 |
| CN | 105592826 A | 5/2016 |
| CN | 105832452 A | 8/2016 |
| DE | 202008014828 U1 | 2/2009 |

(56) References Cited

FOREIGN PATENT DOCUMENTS

| | | |
|---|---|---|
| DE | 102011015995 A1 | 10/2012 |
| DE | 10 2014 113836 A1 | 3/2016 |
| EP | 0701800 A1 | 3/1996 |
| EP | 0894505 A2 | 2/1999 |
| EP | 1488763 A2 | 12/2004 |
| EP | 2545887 A1 | 1/2013 |
| EP | 2 777 642 A1 | 9/2014 |
| EP | 2777638 A1 | 9/2014 |
| EP | 2777649 A1 | 9/2014 |
| EP | 2 915 509 A1 | 9/2015 |
| EP | 2915509 A1 | 9/2015 |
| EP | 3 311 782 A1 | 4/2018 |
| FR | 2939637 A1 | 6/2010 |
| JP | 3-503246 A | 7/1991 |
| JP | 11-57010 A | 3/1999 |
| JP | 11-57020 A | 3/1999 |
| JP | 2004-267750 A | 9/2004 |
| JP | 2013-541358 A1 | 11/2013 |
| JP | 2016-202248 A | 12/2016 |
| WO | 1989/008433 A1 | 9/1989 |
| WO | WO 95/05132 A1 | 2/1995 |
| WO | 99/43379 A1 | 9/1999 |
| WO | 2001/015632 A1 | 3/2001 |
| WO | 01/35864 A1 | 5/2001 |
| WO | 2001/058384 A1 | 8/2001 |
| WO | 2001/072240 A1 | 10/2001 |
| WO | 2005/087138 A1 | 9/2005 |
| WO | 2008/130530 A1 | 10/2008 |
| WO | 2012/082440 A1 | 6/2012 |
| WO | 2012/096687 A1 | 7/2012 |
| WO | 2013/126299 A1 | 8/2013 |
| WO | 2013/151793 A1 | 10/2013 |

OTHER PUBLICATIONS

Ansaar T. Rai et al., "Cerebrovascular geometry in the anterior circulation: an analysis of diameter, length and the vessel taper", J NeuroIntervent Surg 2013; 5: 371-375_ doi: 10_ 1136/neurintsurg-2012-010314; Apr. 4, 2012.
mig-welding.co.uk; Excerpt from with comment of Jun. 29, 2011 on pictures of welds.
mitcale.com; Welded connections excerpt, downloaded Dec. 6, 2012.
Navigate Tough Anatomy; brochure Copyright 2009; Codman & Shurtleff, Inc., 325 Paramount Drive, Raynham, Massachusetts.
Plug Weld Joining Two Plates; Excerpt from esabna.com, downloaded Dec. 6, 2012.
Extended European Search Report issued in EP 19 19 0077 dated Dec. 13, 2019.
Extended European Search Report issued in corresponding European Patent Application No. 19 21 9438 dated Apr. 7, 2020.
Notification of Reasons for Refusal issued in corresponding Japanese Patent Application No. 2020-024204 dated Feb. 2, 2021 (only English translation submitted).
Chinese Office Action and Search Report issued in corresponding Chinese Patent Application No. 201710981691.1 dated Feb. 22, 2021, with English translation of Search Report.
Notification of Reasons for Refusal issued in corresponding Japanese Patent Application No. 2017-190589 dated Jun. 29, 2021, English translation only.

* cited by examiner

SYSTEMS AND METHODS OF USING A BRAIDED IMPLANT

CROSS REFERENCE TO RELATED APPLICATIONS

The present application and U.S. patent application Ser. No. 16/153,517, now U.S. Pat. No. 10,463,510, are both a divisional application of U.S. patent application Ser. No. 16/056,135, now U.S. Pat. No. 10,456,280, filed Aug. 6, 2018. The entire contents of which are hereby incorporated by reference.

FIELD

The present disclosure relates to implants within body vessels and more particularly to flow diverters, stents and related methods that included braided implants formed of strands of material.

BACKGROUND

Vascular disorders and defects such as aneurysms and other arterio-venous malformations are especially difficult to treat when located near critical tissues or where ready access to a malformation is not available. Both difficulty factors apply especially to cranial aneurysms. Due to the sensitive brain tissue surrounding cranial blood vessels and the restricted access, it is very challenging and often risky to surgically treat defects of the cranial vasculature.

Typically, a stent-like vascular reconstruction device is first guided beneath the aneurysm to be treated using a delivery catheter. One commercially available reconstruction product is the CERENOVOUS ENTERPRISE® Vascular Reconstruction Device and System as described, whereby The CERENOVOUS ENTERPRISE® stent device is carried by a central delivery wire and initially held in place on the delivery wire in a collapsed state by a sheath-type introducer. Typically, a delivery catheter such as a PROWLER® SELECT® Plus microcatheter, also commercially available from Cerenovous and as disclosed by Gore et al. in U.S. Pat. No. 5,662,622, for example, is first positioned intravascularly with its distal tip slightly beyond the neck of the aneurysm. The tapered distal tip of the introducer is mated with the proximal hub of the delivery catheter, and the delivery wire is then advanced through the delivery catheter.

The CERENOVOUS ENTERPRISE® stent device has a highly flexible, self-expanding closed cell design with a number of coils of radiopaque wire to serve as markers at each flared end of the device. Manufacture of such markers is relatively time-consuming and expensive due to the small size of the stent and the need to wrap the radiopaque wire multiple times around struts on the stent, which is especially difficult within closed cells of the stent.

Vascular aneurysms have several methods of treatment available. One approach includes flow diverting stents that can be intra-vascular stents dense enough so that blood flow is diverted from entering the aneurysm. Such flow diverters are a recent and growing treatment option. Otherwise, the majority of the current generation of flow diverters are composed of a tubular braid of metal wires that are operate similar to a finger trap toy. These tubular braids are then compressed radially, delivered through a small-bore catheter to the treatment site, and then expanded in place.

Further, the weakness and non-linear nature of the neurovasculature limits the applicability of such stents in procedures, for example, in repairing neurovascular defects. Furthermore, known delivery methods are less useful in vasoocclusive surgery, particularly when tiny vessels, such as those found in the brain, are to be treated. Accordingly, there is a need for braided implants that can be used with delivery techniques in vasoocclusive treatment of neurovascular defects that provides selective reinforcement in the vicinity of the neurovascular defect. There is also a need for a braided stent that reduces trauma or risk of rupture to the blood vessel. The solution of this disclosure resolves these and other issues of the art.

SUMMARY

Disclosed herein are various exemplary devices, systems, and methods of the present disclosure that can address the above needs.

An object of the present solution is to provide one or more braided implants that are configured as flow diverters that provide longer vessel diameter ranges for tapering vessels and maintain the target porosity over a predetermined length (e.g., a 1 mm vessel diameter range).

An object of the present solution is to increase the applicable vessel diameter range for braided implants to minimize the number of devices necessary for practitioners when treating an aneurysm. In one example, the one or more braided implants comprise a broad plateau area of the characteristic porosity curve, indicating the braided implant (s) for vessel diameters within the plateau (resulting in a 1.0 mm wide indicated range), and overlapping the device indicated ranges so the doctor has options for the best choice depending on the anatomy presented.

In certain examples, a braided implant is disclosed that is configured as a flow diverter for treating an aneurysm. The implant can include a braided mesh configured to maintain a substantially consistent target porosity in a tapered vessel over at least a 1 mm vessel diameter range. The braided mesh can also be configured to maintain the substantially consistent target porosity between proximal and distal ends of the braided mesh while in the tapered vessel.

In certain examples, the tapered vessel includes a proximal end diameter and a distal end diameter that differ by up to 1 mm, wherein the up to 1 mm vessel diameter range is defined by comparing the proximal and distal end diameters. However, it is contemplated that the diameter can differ by at least 0.5 mm or any other diameter differential as needed or required.

In certain examples, the substantially consistent target porosity is approximately 70%.

In certain examples, the predetermined length between proximal and distal ends of the braided mesh in the tapered vessel is at least 3 cm.

In certain examples, the predetermined length between proximal and distal ends of the braided mesh in the tapered vessel is at least 2 cm.

In certain examples, the predetermined length between proximal and distal ends of the braided mesh in the tapered vessel is at least 1 cm.

In certain examples, the predetermined length between proximal and distal ends of the braided mesh in the tapered vessel is defined between the proximal cavernous internal carotid artery and the internal carotid artery terminus.

In certain examples, a braided implant is disclosed for medical use. The implant can include a mesh having a proximal end and a distal end, wherein the mesh comprises a porosity substantially consistent between the proximal and distal ends over a 1 mm radial range in vessel diameter.

In certain examples, the porosity is approximately 70% over the 1 mm radial range in vessel diameter.

In certain examples, the braided implant further comprises an indicated vessel diameter, and wherein the braided implant is configured such that the indicated vessel diameter coincides with a peak of a porosity curve of the braided implant. The braided implant can include a porosity plateau that corresponds to the 1 mm radial range in vessel diameter that is disposed about the peak of the porosity curve.

In certain examples, across a vessel diameter range of 2 to 3 mm, a porosity of the braided implant ranges between 65% and 70%.

In certain examples, across a vessel diameter range of 2.5 to 3.5 mm, a porosity of the braided implant ranges between 65% and 70%.

In certain examples, across a vessel diameter range of 3.0 to 4.0 mm, a porosity of the braided implant ranges between 65% and 70%.

In certain examples, across a vessel diameter range of 3.5 to 4.5 mm, a porosity of the braided implant ranges between 65% and 70%.

In certain examples, across the braided implant is configured for a vessel diameter range of 3.5 to 4.5 mm, and wherein the braided implant includes a porosity of 69% at a vessel diameter of 3.5 mm; a porosity of 69% at a vessel diameter of 4.0 mm; and a porosity of 67% at a vessel diameter of 4.5 mm.

In certain examples, across a vessel diameter range of 4.5 to 5.5 mm, a porosity of the braided implant ranges between 65% and 70%.

In certain examples, a pore density of the braided implant is 18 pores/mm$^2$.

In certain examples, a pore density of the braided implant is 23 pores/mm$^2$.

In certain examples, a pore density of the braided implant is 19 pores/mm$^2$.

In certain examples, a pore density of the braided implant is approximately 18 to 23 pores/mm$^2$.

In certain examples, a target vessel treated by the braided implant is tapered.

In certain examples, the braided implant is a substantially cylindrical porous structure.

In certain examples, the braided implant is a stent.

In certain examples, the braided implant is a flow diverter.

In certain examples, the braided implant is formed from a plurality of single strands composed of at least a first material and one or more radiopaque multi-strands.

In certain examples, the braided implant is woven to include at least a second multi-strand.

In certain examples, the braided implant is formed from a plurality of multi-formed of monofilaments each laid together with monofilaments, respectively.

In certain examples, the braided implant further includes a pattern of that is woven, wherein the pattern comprises openings defined by a plurality of single strands oriented in a first direction and by a plurality of single strands oriented in a second direction transverse to the first direction.

In certain examples, the braided implant further includes a pattern of that is braided, wherein the pattern comprises openings defined by a plurality of single strands oriented in a first direction and by a plurality of single strands oriented in a second direction transverse to the first direction.

In certain examples, a system for treating an aneurysm is disclosed. The system can include a plurality of braided implants, wherein each braided implant comprises a porosity substantially consistent over a different 1 mm radial range in vessel diameter, each braided implant configured to provide substantially consistent porosity over different 1 mm diameter ranges.

In certain examples, the braided implant is configured for use in a tapered vessel. The tapered vessel can include a proximal end diameter and a distal end diameter that differ by up to 1 mm. The different 1 mm radial range in vessel diameter can be defined by comparing the proximal and distal end diameters. However, the different 1 mm radial range in vessel diameter can be also determined by measuring the vessel diameter at two separate locations at the treatment site.

In certain examples, the plurality of braided implants of the system is configured to treat any vessel within a 1.5 mm to 6 mm diameter range.

In certain examples, the plurality of braided implants of the system includes a first braided implant (10) configured to treat a vessel diameter range of 2 to 3 mm; a second braided implant (10) configured to treat a vessel diameter range of 2.5 to 3.5 mm; a third braided implant (10) configured to treat a vessel diameter range of 3.0 to 4.0 mm; a fourth braided implant (10) configured to treat a vessel diameter range of 3.5 to 4.5 mm; a fifth braided implant (10) configured to treat a vessel diameter range of 4.0 to 5.0 mm; and a sixth braided implant (10) configured to treat a vessel diameter range of 4.5 to 5.5 mm. The porosity of each braided implant (10) can range between 65% and 70% at the indicated vessel range for the respective implant. In some examples, the porosity of each braided implant is approximately 70%. In some examples, each braided implant further comprises an indicated vessel diameter, and wherein the braided implant is configured such that the indicated vessel diameter coincides with a peak of a porosity curve of the braided implant. In some examples, each braided implant further includes a porosity plateau that corresponds to the 1 mm range in vessel diameter that is disposed about the peak of the porosity curve. In some examples, each braided implant includes a pore density ranging approximately between 18 to 23 pores/mm$^2$.

In some examples, a pore density of the first braided implant is 18 pores/mm$^2$.

In some examples, a pore density of the second braided implant is 23 pores/mm$^2$.

In some examples, a pore density of the third braided implant is 18 pores/mm$^2$.

In some examples, a pore density of the fourth braided implant is 19 pores/mm$^2$.

In some examples, a pore density of the fifth braided implant is 23 pores/mm$^2$.

In some examples, a pore density of the sixth braided implant is 21 pores/mm$^2$. In some examples, the braided implant includes radiopaque materials such as platinum, chromium, cobalt, tantalum, tungsten, gold, silver, and alloys thereof.

In some examples, a system for treating an aneurysm is disclosed. The system can include a plurality of braided implants, wherein each braided implant a porosity substantially consistent over a different 0.5 mm radial range in vessel diameter, each braided implant (10) configured to provide substantially consistent porosity over different 0.5 mm radial diameter ranges. However, other different radial ranges could be used as needed or required with the system, including different vessel diameter ranges of 0.3 mm, 0.4 mm, 0.6 mm, 0.7 mm, 0.8 mm, 0.9 mm, or the like.

In some examples, a method is disclosed for treating an aneurysm. The method can include determining a vessel diameter associated with a vessel of the aneurysm; selecting one of a plurality of braided implants for treating the vessel (e.g., based on the determined vessel diameter), wherein each braided implant includes a porosity substantially consistent over at least a 1 mm vessel diameter range, each braided implant configured to provide substantially consistent porosity over different 1 mm diameter ranges; and treating the vessel with the one of the plurality of braided implants.

In some examples, the vessel is tapered and includes a proximal end diameter and a distal end diameter that differ by up to 1 mm, wherein the determining the vessel diameter includes comparing the proximal and distal end diameters or diameters.

In some examples, the vessel is tapered and has approximately 1 mm vessel diameter differential, the method further includes maintaining the substantially consistent porosity across the approximately 1 mm vessel diameter differential.

In some examples, the method includes configuring each braided implant to cover a vessel diameter range with 0.5 mm overlap between each respective other braided implant.

In some examples, the vessel diameter is tapered and ranges between approximately 3-4 mm.

In some examples, the vessel diameter is tapered and ranges between approximately 3.5-4.5 mm.

In some examples, the vessel diameter is tapered and ranges between approximately 4-5 mm.

In some examples, the vessel diameter is tapered and ranges between approximately 4.5-5.5 mm.

In some examples, the vessel diameter is tapered and ranges between approximately 5.0-6.0 mm.

In some examples, the vessel diameter is tapered and the plurality of braided implants is configured to treat vessel diameters ranging between 1.5-6 mm.

In some examples, the determining a vessel diameter is implemented by X-ray, fluoroscopy, MRI, or other visualization means In some examples, the treating the vessel includes advancing the braided implant to an aneurysm; and reconstructing blood flow in the vessel by excluding the aneurysm and diverting blood flow from the aneurysm using the one of the plurality of braided implants.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The above and further aspects of this solution are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

Figure 1:
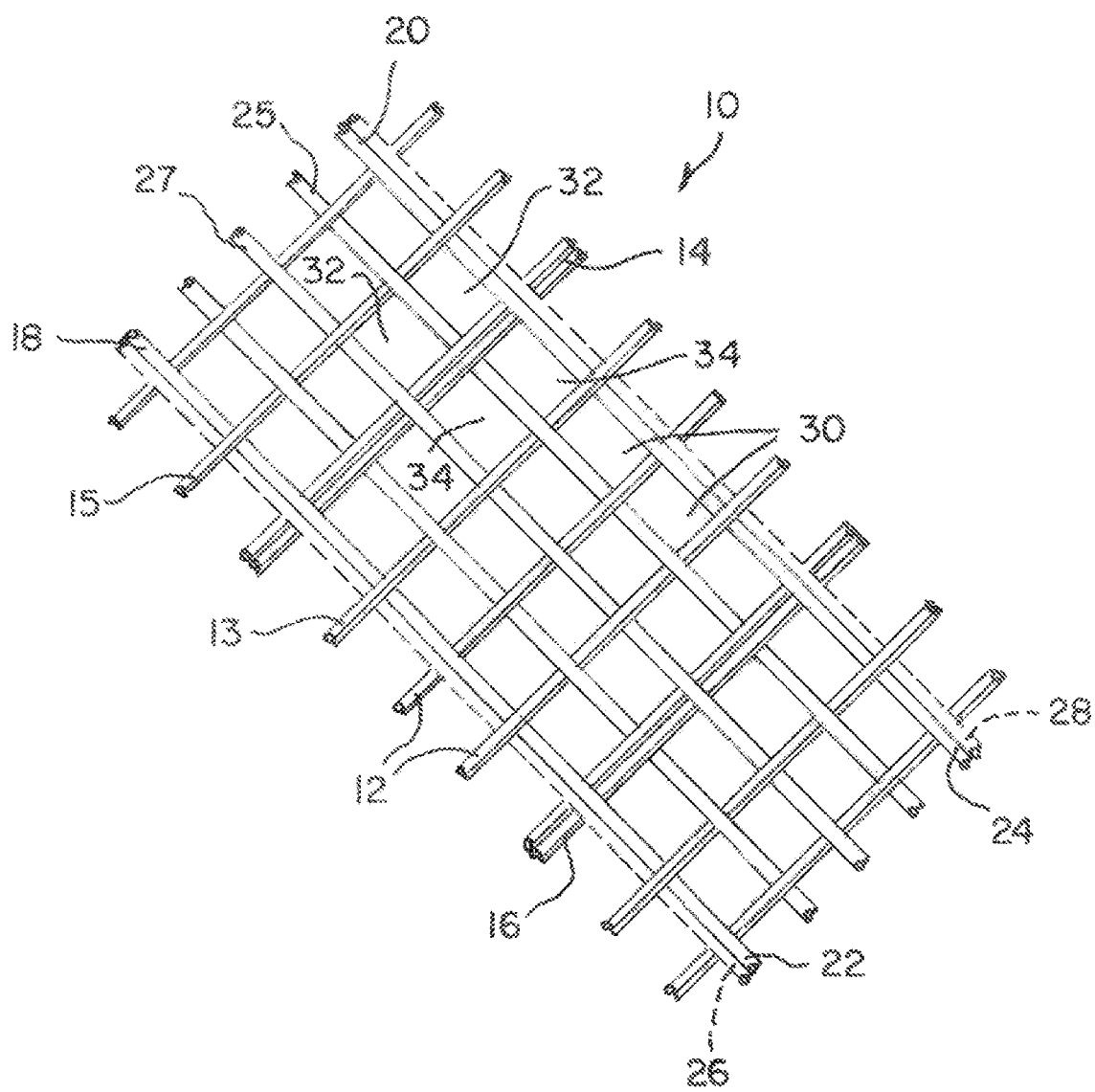
FIG. 1 is a schematic enlarged view of a portion of an implant body formed of single strands and one or more radiopaque multi-strands according to the present invention.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" may be vasculature of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a braid body to the vasculature of a subject.

As discussed herein, "strand" is intended in its broadest meaning to include a wire, a fiber, a filament, or other single elongated member.

As discussed herein, "radiopaque" is utilized for its normal meaning of being radiodense, that is, formed of one or more materials which inhibit the passage of electromagnetic radiation to increase visibility during imaging. Suitable radiopaque materials for use according to the present invention include platinum, chromium, cobalt, tantalum, tungsten, gold, silver, and alloys thereof.

The braided implants 10 of this disclosure can be better understood when looking at the figures appended to this disclosure. For instance, in FIG. 1, a schematic enlarged view of a portion of a braided implant 10 is shown according to an example of this disclosure. Braided implant 10 can be formed of single strands 12 composed of at least a first material and one or more radiopaque multi-strands 14. In this construction, implant 10 is woven to include at least a second multi-strand 16. In another construction, indicated by dashed lines, the implant 10 further includes multi-strands 18 and 20 formed of monofilaments 22 and 24 each laid together with monofilaments 26 and 28, respectively. The pattern of implant 10, which is woven in some constructions and braided in other constructions, includes openings 30 defined by single strands 12 oriented in a first direction and by single strands 24 and 25 oriented in a second direction that is transverse to the first direction, for example. Implant 10 further includes openings 32 and 34 defined on either side of multi-strand 14 by single strands 13 and 15 oriented in the same direction as multi-strand 14 and by single strands 24, 25 and 27 oriented in a transverse direction. In some constructions, openings 32 and 34 are slightly larger than openings 30 which are defined only by single strands; in other constructions, all openings 30, 32 and 34 are substantially the same.

Other embodiments are contemplated for implants 10 of this disclosure and can also be observed in U.S. Pat. Pub. 2016/0058524, a reference that is incorporated in its entirety herein. Braided implant 10 constructions of this disclosure in some examples are considered to have substantially the same pattern as if implant 10 were formed solely from single strands of material. Since the multi-strands are braided, woven or otherwise laid in parallel to each other in the same manner as if single strands of radiopaque material were utilized, and especially when each filament of the multi-strand has the same diameter as the single strands, there is little or no mechanical impact to the performance of the implant, such as flexibility, ability to expand, and crimped profile.

Figure 2:
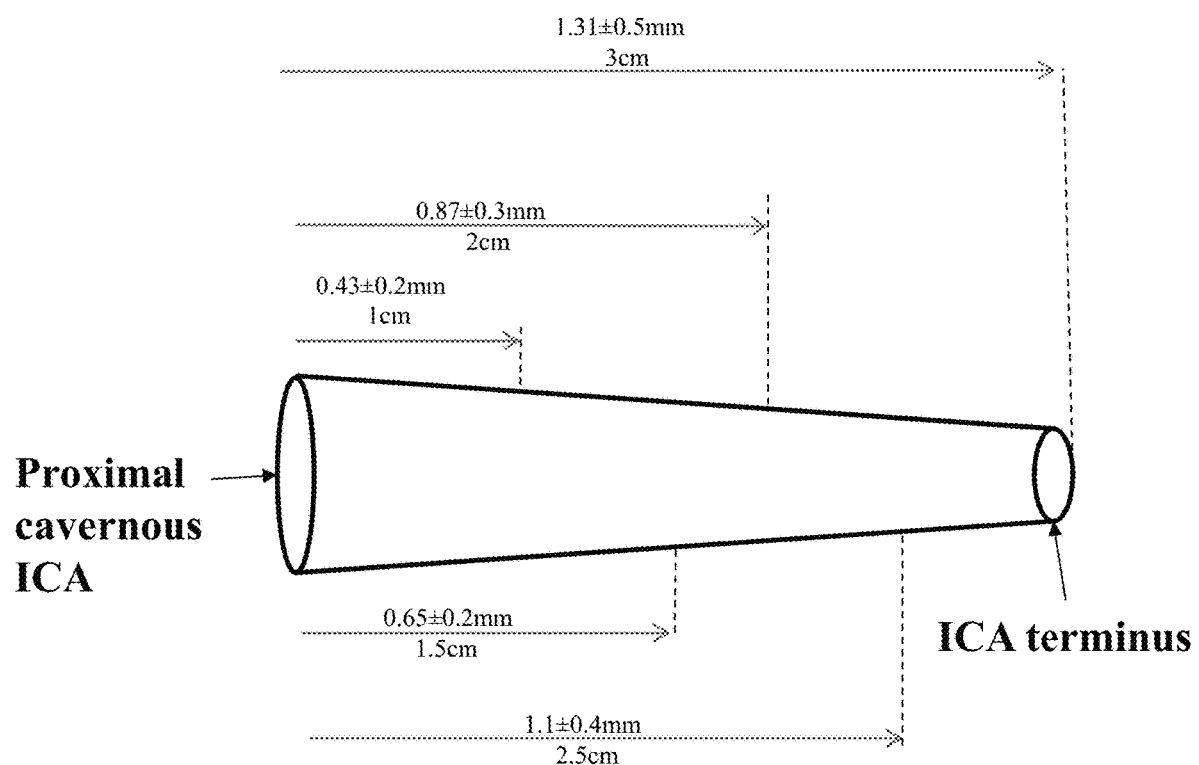
FIG. 2 depicts a side plan view of an example vessel contemplated for use with the braided implant of this disclosure.

Turning to FIG. 2, a side plan view of an example vessel is shown that is contemplated for use with implant 10 of this disclosure. As can be seen, the example vessel tapers along its longitudinal axis of the internal carotid artery (ICA). See, Rai A T, Hogg J P, Cline B, et al. J NeuroIntervent Surg (2012) which is incorporated by reference in its entirety. The Rai study undertook to determine the typical length, diameter and taper of vessels in the anterior cerebral circulation. The arterial diameter was measured at the proximal cavernous ICA, the ICA terminus, the middle cerebral artery MCA origin and an M2 origin. The length between these endpoints was calculated along the center line. The vessel taper was calculated for the ICA as the change in caliber per unit length. In carrying out this study, the Rai study determined that the mean diameter at the cavernous ICA and the ICA terminus was 5±0.6 mm and 3.6±0.4 mm, respectively. The mean ICA taper was 0.04±0.02 mm/1 mm. For the MCA, the diameter at the MCA and M2 origins measured 3.1±0.4 mm and 2.4±0.4 mm, respectively.

FIG. 2 provides non-limiting examples of diameter measurements at respective lengths taken from the proximal cavernous ICA towards the ICA terminus further exemplifying the tapering nature of the vessel. The Rai study confirmed that the ICA tapers from its proximal cavernous segment to the ICA terminus that implant 10 is configured to treat.

Figure 3:
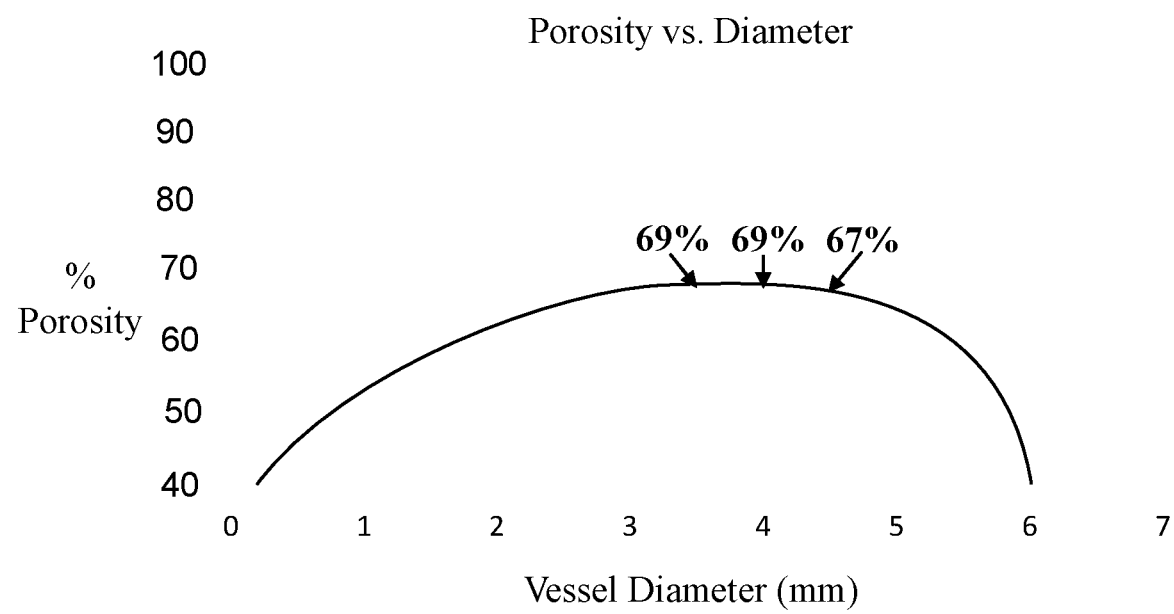
FIG. 3 is a graph that shows porosity versus vessel diameter for an example braided implant of this disclosure.

Turning to FIG. 3, a graph is provided that shows the percent porosity of an example braided implant 10 of this disclosure as compared to vessel diameter that were investigated for this disclosure. As can be seen, the braided implant 10 of this disclosure held a relatively consistent pore size and porosity over a 1 mm vessel diameter range. Throughout this disclosure, when referring to a vessel diameter range, it is intended that this term means a range of diameters as measured between two separate locations in the vessel being treated by braided implant 10. For example, a practitioner using X-ray visualization could measure the vessel diameter of the proximal cavernous ICA as 4.2 mm whereas the vessel diameter towards the ICA terminus could be 3.2. In this respect, the vessel diameter range in this example tapered vessel would be 1 mm. The implants 10 of this disclosure are designed to accommodate such tapering vessels across these example vessel diameter ranges while also maintaining a substantially consistent target porosity. This is particularly advantageous since it means fewer implants are required to accommodate vessels that tapering greater than conventional devices (e.g., vessel diameter ranges of approximately 0.25 mm) or tortuosity typically seen in the neurovasculature.

With this, FIG. 3 depicts an example vessel having a 1 mm vessel diameter range between 3.5 mm to 4.5 mm. In this example, the braided implant 10 of this disclosure maintained approximately 70% porosity. Specifically, at a diameter of 3.5 mm, the porosity of the braid was approximately 69%. At a diameter of 4.0 mm, the porosity of the braid was approximately 69%. At a diameter of 4.5 mm, the porosity of the braid was approximately 67%.

Figure 4:
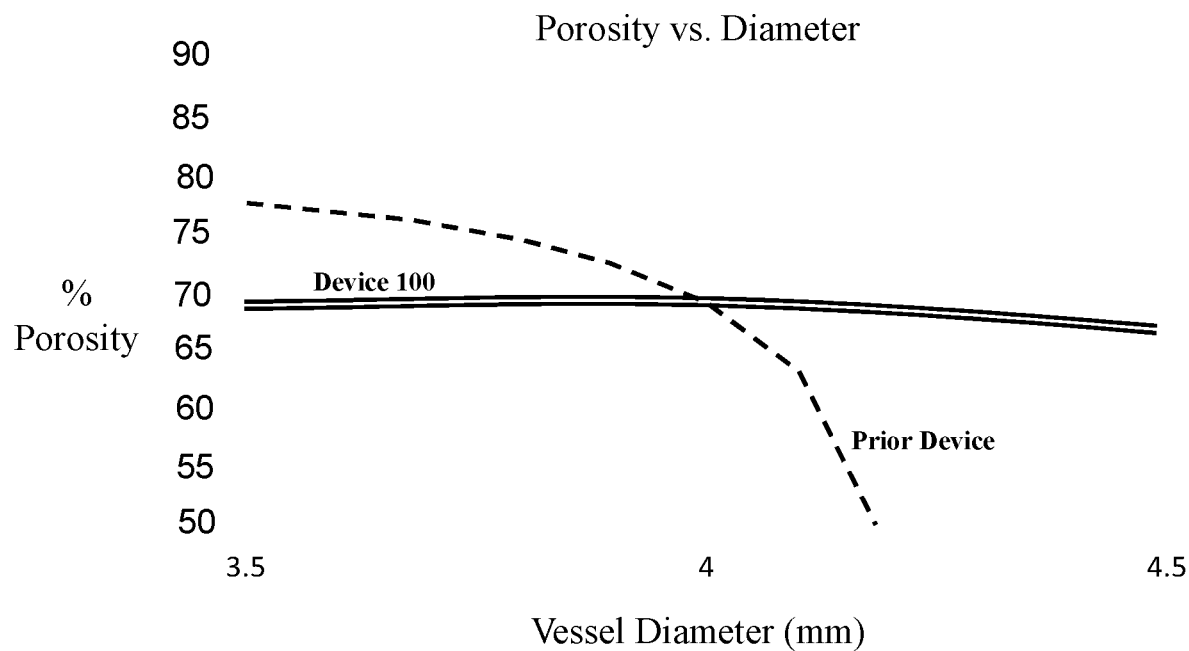
FIG. 4 is a graph that compares the porosity versus vessel diameter for an example braided implant of this disclosure versus a conventional device.

Turning to FIG. 4, a graph is provided that summarizes a comparison carried out whereby the porosity versus vessel diameter is shown for an example implant 10 of this disclosure versus the Pipeline™ Embolization Device (PED) by Medtronic across a 1 mm vessel diameter range. Specifically, braided implant 10 and the PED device were compared between a vessel diameter range of 3.5 mm to 4.5 mm. As can be seen, the braided implant 10 of this disclosure held a relatively consistent pore size and porosity over a 1 mm vessel diameter range at about 70% across the same range previously shown in FIG. 3. Conversely, the PED device at 3.5 mm vessel diameter demonstrated 80% porosity, at 4 mm vessel diameter demonstrated a 70% porosity, and at 4.5 mm vessel diameter demonstrated less than 50% porosity. Stated differently, the porosity of the PED device diminished appreciably as the diameter of the vessel increased across the 1 mm range, whereas the example braided implant 10 of this disclosure demonstrated a substantially consistent porosity over the 1 mm diameter range.

FIG. 4 also shows the porosity of each device as it changes while expanding and it is characteristically the same. In certain examples, the braided implant 10 is designed such that the indicated vessel diameter coincides with the peak of the porosity curve and the plateau area around it (which deviates from the target porosity very little). For example, in FIG. 3 the braided implant 10 shown is indicated for an artery diameter range from 3.5 mm to 4.5 mm. This device remains very close to the target porosity of 70% throughout its expansion range, which has a width of 1.0 mm.

When the device is compressed, for example, it is dense so its porosity is very low (see, e.g., the lower-left of FIG. 3). As the device expands, the porosity increases since the pores of the braided implant 10 are opening. At a certain point, the porosity reaches a peak, which is when the braiding angle is at 90 degrees since each pore can be a square, and as large as it can get, shown at the center arrow of FIG. 3. Further expansion of the diameter past this peak then reduces the size of each pore and thus the porosity. When the braided implant 10 reaches maximum diameter at its expansion limit, then braided implant 10 is again very dense and porosity is correspondingly low (see, e.g., lower-right of FIG. 3).

In contrast, other devices known might be designed differently, so that the plateau area of the porosity curve is not as wide as 1.0 mm, or they might be indicated for artery diameters that do not coincide with the plateau area. In these older approaches, the range of diameters that coincide with the target porosity would be narrow since outside the plateau, small changes in artery diameter result in large deviations from the target porosity. Accordingly, other devices known would be incapable of being able to treat a wider range of vessel diameters.

Figure 5:
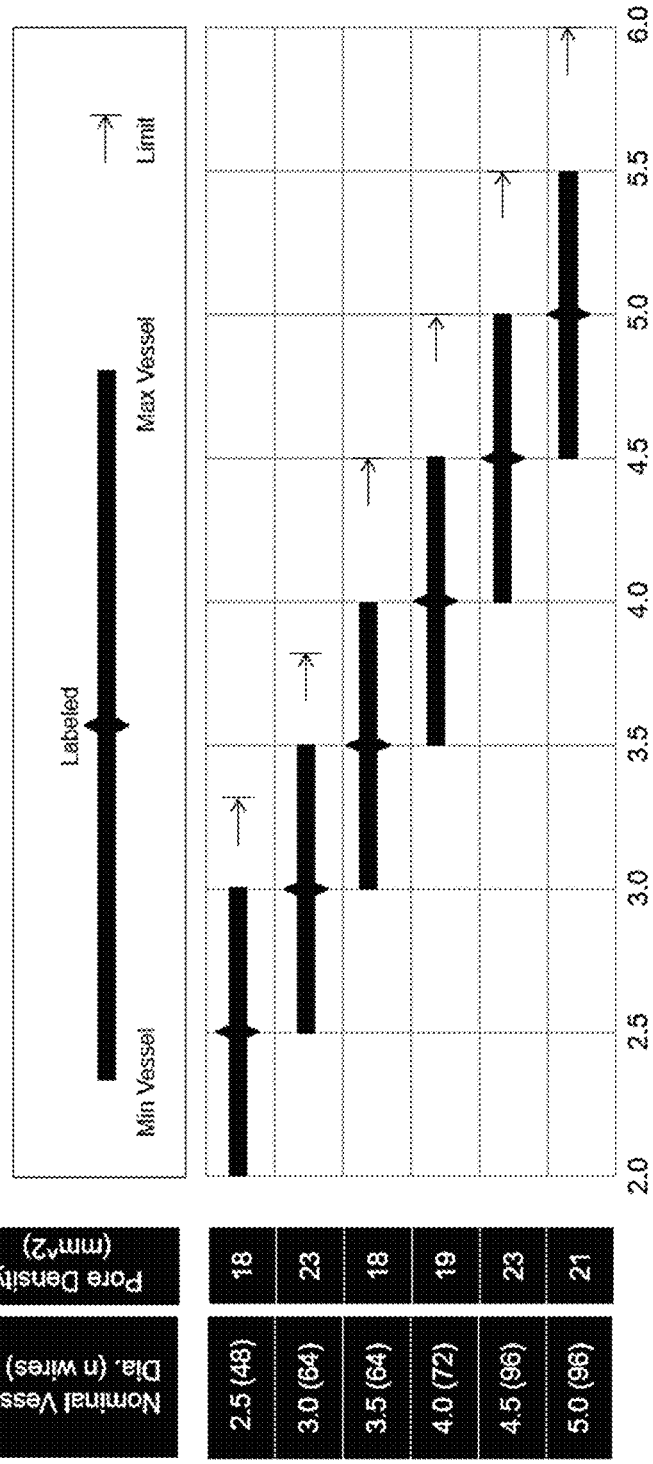
FIG. 5 is a graph that shows the pore density and number of wires versus vessel diameter for a set of example braided implants of this disclosure.

Turning to FIG. 5, a graph is provided that summarizes the porosity versus vessel diameter for an example braided implant 10 of this disclosure. Specifically, FIG. 5 shows six separate braided implants (10) that each have approximately a 1 mm range in vessel diameter, and offset from one another by approximately half of that range (0.5 mm). The legend shows the range of vessel diameters from minimum to maximum and corresponding label for the applicable braided implant (10). For example, a first braided implant (10) is configured for a vessel diameter range between 2.0 mm and 3.0 mm with a label of 2.5 mm. The first braided implant (10) has 48 wires with a pore density (mm$^2$) of 18. A second braided implant (10) is configured for a vessel diameter range between 2.5 mm and 3.5 mm with a label of 3 mm. The second braided implant (10) has 64 wires with a pore density (mm$^2$) of 23. A third braided implant (10) is configured for a vessel diameter range between 3.0 mm and 4.0 mm with a label of 3.5 mm. The third braided implant (10) has 64 wires with a pore density (mm$^2$) of 18. A fourth braided implant (10) is configured for a vessel diameter range between 3.5 mm and 4.5 mm with a label of 4.0 mm. The fourth braided implant (10) has 72 wires with a pore density (mm$^2$) of 19. A fifth braided implant (10) is configured for a vessel diameter range between 4.0 mm and 5.0 mm with a label of 4.5 mm. The fifth braided implant (10) has 96 wires with a pore density (mm$^2$) of 21. A sixth braided implant (10) is configured for a vessel diameter range between 4.5 mm and 5.5 mm with a label of 5 mm. The sixth braided implant (10) has 96 wires with a pore density (mm$^2$) of 21.

Figure 6:
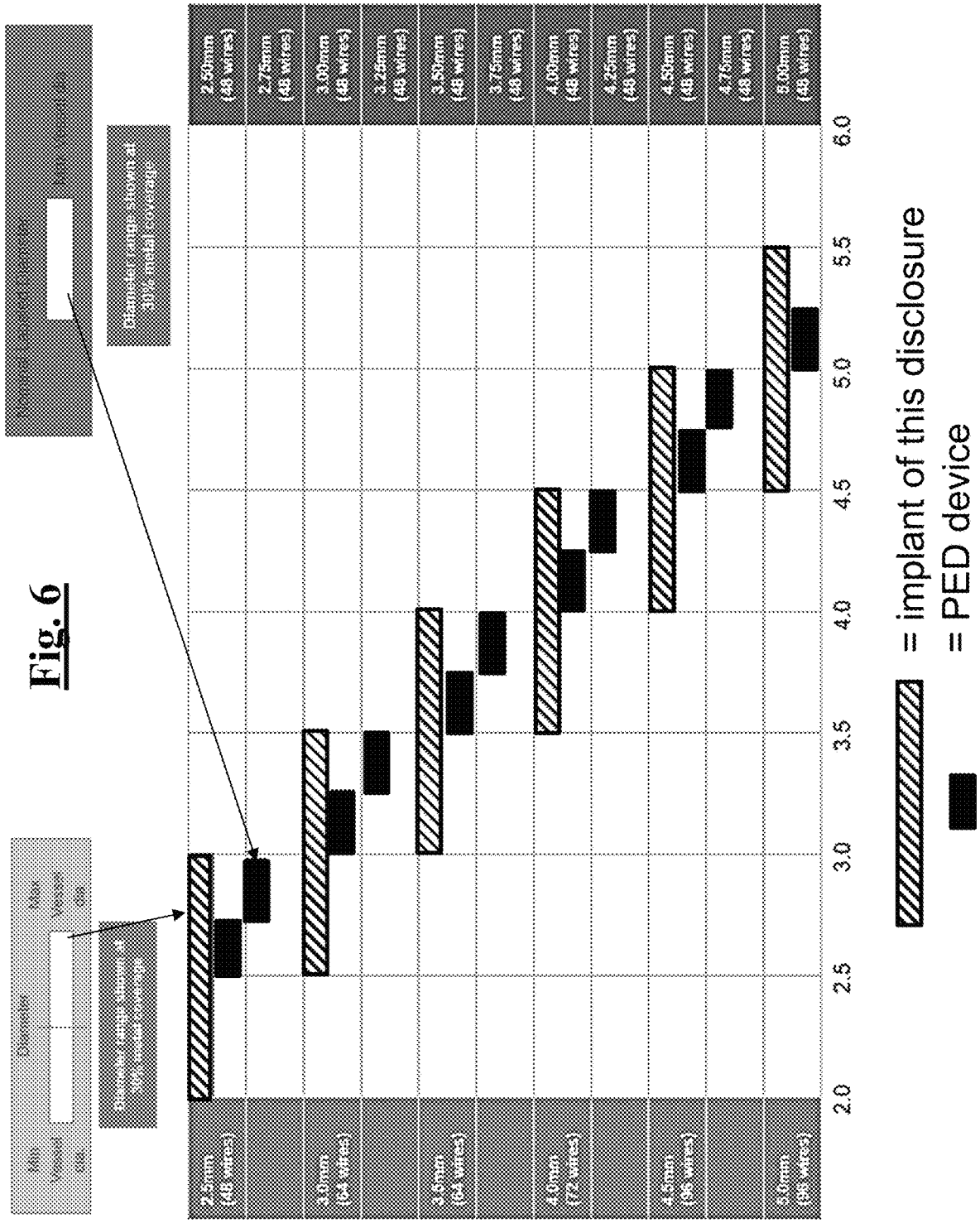
FIG. 6 is a graph that compares the porosity versus vessel diameter for a set of example braided implants of this disclosure versus a set of conventional devices.

Turning to FIG. 6, a graph is provided that summarizes a comparison carried out whereby the porosity versus vessel diameter is shown for set of example implants (10) of this disclosure versus a set of PED devices across different vessel diameter ranges, including from 2 mm to 6 mm. Specifically, in the first braided implant 10 indicated as being configured for use across a vessel diameter of 2 mm to 3 mm, braided implant 10 was observed as providing approximately 70% porosity, whereas a comparable PED device was only able to maintain approximately 70% porosity across a vessel diameter of 2.5 mm to 2.75 mm (i.e. only a 0.25 mm vessel diameter range). Another PED device in the relevant diameter range was necessary for said PED device just to complete the gap from 2.75 mm to 3.0 mm vessel diameter range, as shown. The first braided implant (10) was constructed from 48 strands of wire and the PED device was similarly constructed from 48 strands of wire. For the 2.0 mm to 2.5 mm range, two more PED devices would also be required, since the PED device only demonstrated a 0.25 mm range capable of maintaining 70% porosity during use.

FIG. 6 also depicts that a second braided implant (10) indicated as being configured for use across a vessel diameter of 2.5 mm to 3.5 mm, braided implant (10) was observed as providing approximately 70% porosity, whereas a comparable PED device was only able to maintain approximately 70% porosity across a vessel diameter of 3.0 mm to 3.25 mm (i.e. only a 0.25 mm vessel diameter range). The second braided implant (10) in this example was constructed from 64 strands of wire while the PED device was constructed from 48 strands of wire. In other words, at a vessel diameter of 3 mm, the second braided implant (10) used approximately 21.3 strands/mm of vessel diameter while the PED device used 16 strands/mm of vessel diameter. As a result of using fewer strands per diameter, the PED device has a porosity vs diameter curve that has a narrower plateau section than the second braided implant (10). Further, another PED device in the relevant diameter range was necessary for said PED device just to complete the gap from 3.25 mm to 3.50 mm vessel diameter range, as shown. Further, as shown with respect to the 2.5 mm to 3.0 mm range and the first braided implant (10), two more PED devices would also be required, since the PED device only demonstrated a 0.25 mm range capable of maintaining 70% porosity during use.

FIG. 6 also depicts that a third braided implant (10) indicated as being configured for use across a vessel diameter of 3.0 mm to 4.0 mm, braided implant (10) was observed as providing approximately 70% porosity, whereas a comparable PED device was only able to maintain approximately 70% porosity across a vessel diameter of 3.5 mm to 3.75 mm (i.e. only a 0.25 mm vessel diameter range). The third braided implant (10) in this example was constructed from 64 strands of wire while the PED device was constructed from 48 strands of wire. In other words, at a vessel diameter of 3.5 mm, the third braided implant (10) used approximately 18.3 strands/mm of vessel diameter while the PED device used 13.7 strands/mm of vessel diameter. As a result of using fewer strands per diameter, the PED device has a porosity vs diameter curve that has a narrower plateau section than the third braided implant (10). Further, another PED device in the relevant diameter range was necessary for said PED device just to complete the gap from 3.75 mm to 4.00 mm vessel diameter range, as shown.

FIG. 6 also depicts that a fourth braided implant (10) indicated as being configured for use across a vessel diameter of 3.5 mm to 4.5 mm, braided implant (10) was observed as providing approximately 70% porosity, whereas a comparable PED device was only able to maintain approximately 70% porosity across a vessel diameter of 4.0 mm to 4.25 mm (i.e. only a 0.25 mm vessel diameter range). The fourth braided implant (10) in this example was constructed from 72 strands of wire while the PED device was constructed from 48 strands of wire. In other words, at a vessel diameter of 4 mm, the fourth braided implant (10) used approximately 18 strands/mm of vessel diameter while the PED device used 12 strands/mm of vessel diameter. As a result of using fewer strands per diameter, the PED device has a porosity vs diameter curve that has a narrower plateau section than the fourth braided implant (10). Further, another PED device in the relevant diameter range was necessary for said PED device just to complete the gap from 4.25 mm to 4.50 mm vessel diameter range, as shown.

FIG. 6 also depicts that a fifth braided implant (10) indicated as being configured for use across a vessel diameter of 4.0 mm to 5.0 mm, braided implant (10) was observed as providing approximately 70% porosity, whereas a comparable PED device was only able to maintain approximately 70% porosity across a vessel diameter of 4.5 mm to 4.75 mm (i.e. only a 0.25 mm vessel diameter range). The fifth braided implant (10) in this example was constructed from 96 strands of wire while the PED device was constructed from 48 strands of wire. In other words, at a vessel diameter of 4.5 mm, the fifth braided implant (10) used approximately 21.3 strands/mm of vessel diameter while the PED device used 10.7 strands/mm of vessel diameter. As a result of using fewer strands per diameter, the PED device has a porosity vs diameter curve that has a narrower plateau section than the fifth braided implant (10). Further, another PED device in the relevant diameter range was necessary for said PED device just to complete the gap from 4.75 mm to 5.00 mm vessel diameter range, as shown.

FIG. 6 also depicts that a sixth braided implant (10) indicated as being configured for use across a vessel diameter of 4.5 mm to 5.5 mm, braided implant (10) was observed as providing approximately 70% porosity, whereas a comparable PED device was only able to maintain approximately 70% porosity across a vessel diameter of 5.0 mm to 5.25 mm (i.e. only a 0.25 mm vessel diameter range). The sixth braided implant (10) in this example was constructed from 96 strands of wire while the PED device was constructed from 48 strands of wire. In other words, at a vessel diameter of 5.0 mm, the sixth braided implant (10) used approximately 19.2 strands/mm of vessel diameter while the PED device used 9.6 strands/mm of vessel diameter. As a result of using fewer strands per diameter, the PED device has a porosity vs diameter curve that has a narrower plateau section than the sixth braided implant (10). Further, another PED device in the relevant diameter range was necessary for said PED device just to complete the gap from 5.25 mm to 5.50 mm vessel diameter range, as shown.

As seen in FIG. 6, for each indicated 1 mm vessel range covered by one of braided implants (10), four separate PED devices would be required by the practitioner for similar coverage in corresponding vessels, which is both inconvenient, wasteful, but quite possibly unsafe given the nature of blood vessels afflicted with hemorrhagic events and tendencies to taper considerably. For example, if a vessel were to taper more than 0.25 mm, then no current PED device would adequately treat the afflicted vessel in a manner than maintains a substantially consistent target porosity of 70%.

Figure 7:
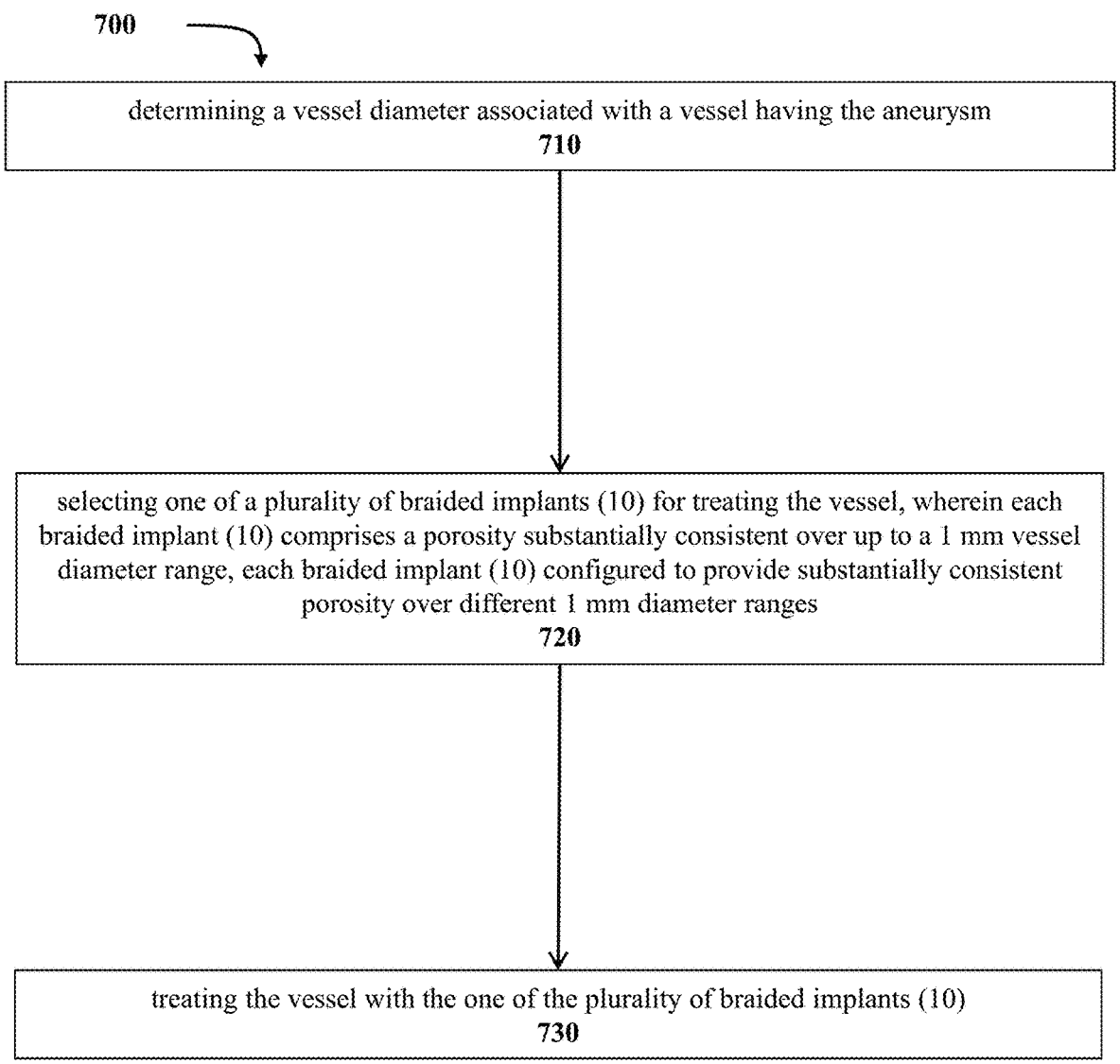
FIG. 7 depicts a flow diagram outlining example method steps of this disclosure.

In FIG. 7, a flow diagram depicts one example method 700 and corresponding steps. Step 710 includes determining a vessel diameter associated with a vessel having the aneurysm. Step 720 includes selecting one of a plurality of braided implants (10) for treating the vessel, wherein each braided implant (10) comprises a porosity substantially consistent over up to a 1 mm vessel diameter range, each braided implant (10) configured to provide substantially consistent porosity over different 1 mm diameter ranges. Step 730 includes treating the vessel with the one of the plurality of braided implants (10).

Figure 8:
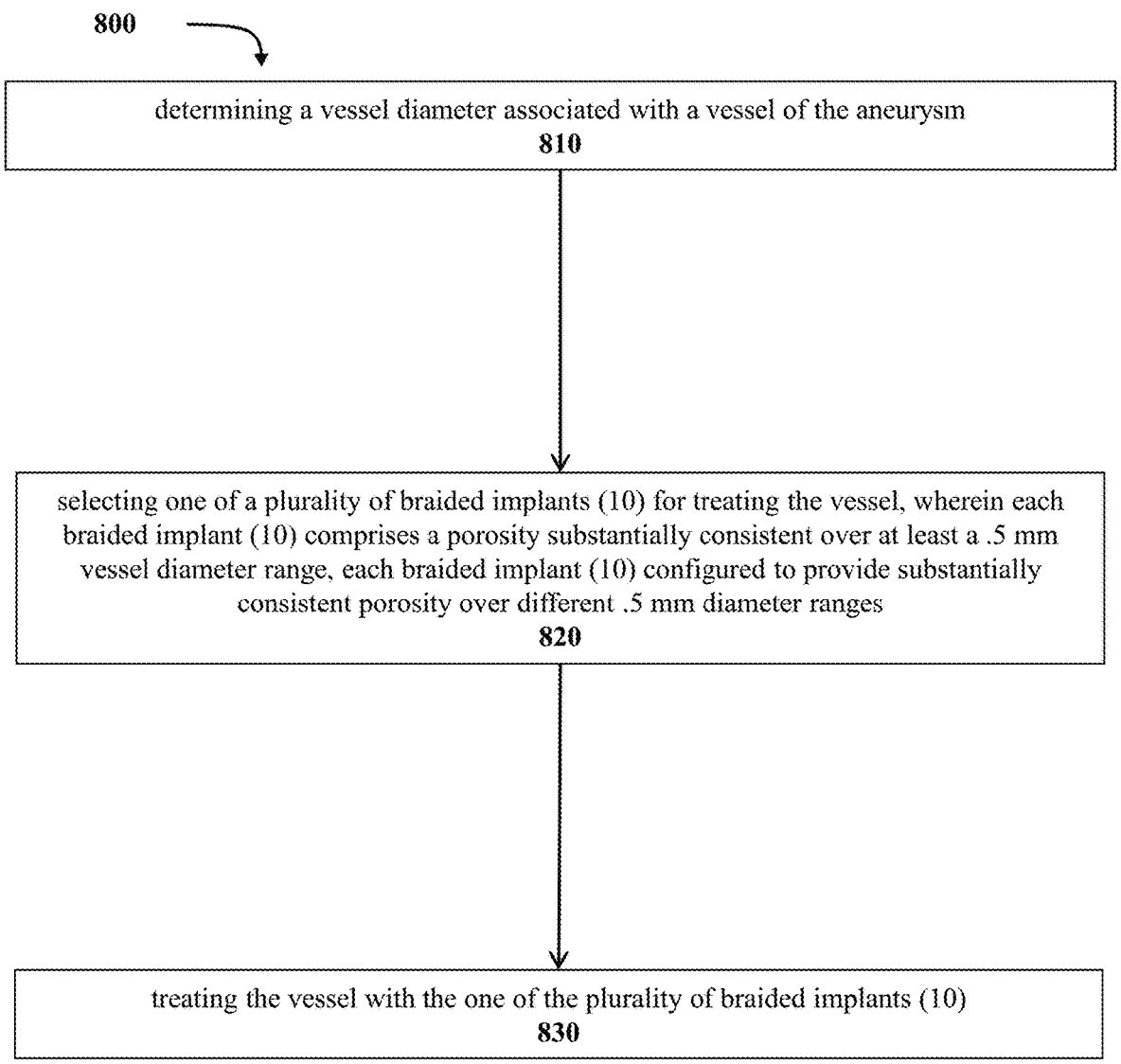
FIG. 8 depicts a flow diagram outlining example method steps of this disclosure.

In FIG. 8, a flow diagram depicts one example method 800 and corresponding steps. Step 810 includes determining a vessel diameter associated with a vessel containing the aneurysm. Step 820 includes selecting one of a plurality of braided implants (10) for treating the vessel, wherein each braided implant (10) comprises a porosity substantially consistent over at least a 0.5 mm vessel diameter range, each braided implant (10) configured to provide substantially consistent porosity over different 0.5 mm diameter ranges. Step 830 includes treating the vessel with the one of the plurality of braided implants (10).

The braided implants (10) of this disclosure are particularly advantageous since a doctor can benefit from a wider indicated diameter range since it can afford some forgiveness for measurement inaccuracies and/or errors (e.g. an artery is measured on X-ray or any other visualization means to be 3.3 mm when it is actually 3.5 mm). Doctors can also benefit since a wider indicate diameter range can maintain consistent porosity close to the target porosity in tapering vessels, which is common. The implant (10) of this disclosure is also advantageous since the anatomical range of artery diameters can be treated with fewer devices, simplifying the device selection process and saving storage space for the inventory they must keep on hand.

In certain examples, a set or family of implants (10) is disclosed, each with a 1.0 mm wide indicated diameter range, are arranged such that they cover the anatomical range with 0.5 mm overlap, as shown in FIGS. 5-6. It is noted that the ranges depicted and described throughout reference a vessel diameter range of up to 1 mm for a respective braided implant (10). However, it is contemplated that the braided implant (10) can be adapted for more than a 1 mm vessel diameter range. The braided implants (10) of this disclosure are s particularly advantageous since for any given artery diameter, there exists two different options of a device that can be selected. For example, an artery with a diameter of 3.25 mm can be at a desired treatment location in the vasculature. If the artery tapers down as you move away from the treatment location (i.e. becomes smaller), then the doctor could select the smaller implant from the set or family of implants by, for example, selecting an implant listed at 2.5 mm, rather than 3.5 mm. In this respect, the artery segment is exposed to target porosity over a longer length. Conversely, if the artery tapers up as you move away from the treatment location (i.e. becomes larger), then the doctor could select the larger implant from the set or family by, for example, selecting an implant listed at 3.0 mm to 4.0 mm. In this respect, similar to the previous example, the artery segment is exposed to the target porosity over a longer length.

The advantages in the present disclosure result from providing a braided implant with a broad plateau area of the characteristic porosity curve so that implant or the family or set of implants is capable of treating artery diameters within the plateau of an approximate 1.0 mm wide indicated range, and overlapping the indicated diameter ranges so the doctor has options for the best choice depending on the anatomy presented.

In certain examples, each of the side-by-side filaments of the braided implants of this disclosure include a monofilament of radiopaque material. In one construction, the carrier having the multi-strand is substantially the same as the carriers for the single strands. Each of the side-by-side filaments of the multi-strand is a monofilament of radiopaque material. Preferably, the diameter of each side-by-side filament is substantially the same as the diameter of the single strands. Forming the body includes establishing a first spacing pattern, such as an open braid pattern or an open weave pattern, and a first wall thickness, and each multi-strand joins in the first spacing pattern without substantial deviation from that pattern and without substantially altering the first wall thickness.

In certain techniques, at least one multi-strand carrier is utilized for every dozen single-strand carriers. Some machines have at least 42 carriers, such as 48 carriers, and at least 6 of the carriers, such as 8 carriers, are loaded with the multi-strands of radiopaque material. This still results in a 48-carrier braid but having double the number of radiopaque strands as when the 8 carriers are loaded with single strands of radiopaque material.

Braided implants of this disclosure, including flow diverters, can be designed for a specific percentage of coverage area per artery area or inversely, the percentage of open area remaining per artery area, known in this disclosure as "porosity", after they have been delivered and expanded in place at the treatment site. The designed porosity can be adjusted by the braiding parameters, such as number of wires, width of wires, braided diameter, and braiding angle which can be alternatively measured as PPI or pitch. Once the target porosity is identified based on these factors, the braid design can be adjusted so that it reaches the target porosity when expanded to the indicated artery diameter.

Braided implants of this disclosure, including flow diverters, can have many variants within a set or family that reach the target porosity at different artery diameters. Therefore, the set or family of devices together allow the physician to treat any diameter artery within the anatomical range (1.5 mm to 6 mm is typical for neurovascular).

The descriptions contained herein are examples illustrating the various embodiments and are not intended to limit the scope of the disclosure. As described herein, the invention contemplates many variations and modifications of a system, device, or method that can be used. Variations can include but are not limited to alternative geometries of elements and components described herein, utilizing any of numerous materials for each component or element (e.g. radiopaque materials, memory shape metals, etc.). These modifications would be apparent to those having ordinary skill in the art to which this invention relates and are intended to be within the scope of the claims which follow.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A method of treating an aneurysm, the method comprising:
   determining a diameter associated with a vessel having the aneurysm, the vessel being tapered up to a 1 mm diameter range;
   selecting one of a plurality of braided implants for treating the vessel, wherein each braided implant comprises a porosity of 65%-70% that is consistent over the up to a 1 mm diameter range, each braided implant configured to provide consistent porosity over different 1 mm diameter ranges; and
   treating the vessel with the one of the plurality of braided implants.

2. The method of claim 1, wherein the tapered vessel comprises a proximal diameter and a distal diameter that differ by up to 1 mm, wherein the determining the vessel diameter comprises comparing the proximal and distal end diameters, the method further comprising:
   maintaining the consistent porosity across the tapered braided implant.

3. The method of claim 1, wherein the treating the vessel comprises:
   advancing the braided implant to an aneurysm; and
   reconstructing blood flow in the vessel by excluding the aneurysm and diverting blood flow from the aneurysm using the selected one of the plurality of braided implants.

4. The method of claim 1, the vessel is tapered and the diameter of the vessel ranges between 3-4 mm.

5. The method of claim 1, the vessel is tapered and the diameter of the vessel ranges between 3.5-4.5 mm.

6. The method of claim 1, the vessel is tapered and the diameter of the vessel ranges between 4-5 mm.

7. The method of claim 1, the vessel is tapered and the diameter of the vessel ranges between 4.5-5.5 mm.

8. The method of claim 1, the vessel is tapered and the plurality of braided implants is configured to treat vessel diameters ranging between 1.5-6 mm.

9. The method of claim 1, the step of determining the diameter is implemented by X-ray, fluoroscopy, or MRI.

10. The method of claim 1, wherein a predetermined length between proximal and distal ends of at least one of the braided implants is at least 3 cm.

11. The method of claim 1, wherein a predetermined length between proximal and distal ends of at least one of the braided implants is at least 1 cm.

12. The method of claim 1, further comprising:
    providing, for each braided implant, an indicated diameter that coincides with a peak of a porosity curve of the respective braided implant.

13. The method of claim 12, further comprising:
    corresponding a porosity plateau to the 1 mm diameter range disposed about the peak of the porosity curve.

14. The method of claim 1, wherein a pore density of each braided implant is 18 to 23 pores/mm$^2$.

15. The method of claim 1, wherein at least one of the braided implants is a cylindrical porous structure.

16. The method of claim 1, further comprising:
    forming at least one of the braided implants from a plurality of single strands composed of at least a first material and one or more radiopaque multi-strands.

17. The method of claim 1, further comprising:
    forming at least one of the braided implants of monofilaments each laid together with monofilaments, respectively.

18. The method of claim 1, wherein the 1 mm diameter range of each of the plurality of braided implants overlaps with the 1 mm diameter ranges of at least one other braided implant of the plurality of braided implants.

19. The method of claim 1, wherein the 1 mm diameter range of each of the plurality of braided implants overlaps with the 1 mm diameter ranges of at least one other braided implant of the plurality of braided implants by 0.5 mm.

20. The method of claim 16, wherein the strands of the multi-strands are parallel to each other.

\* \* \* \* \*